(12) United States Patent
Yost et al.

(10) Patent No.: US 7,491,169 B2
(45) Date of Patent: *Feb. 17, 2009

(54) ULTRASONIC APPARATUS AND METHOD TO ASSESS COMPARTMENT SYNDROME

(75) Inventors: William T. Yost, Newport News, VA (US); Toshiaki Ueno, San Diego, CA (US); Alan R. Hargens, San Diego, CA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 547 days.

This patent is subject to a terminal disclaimer.

(21) Appl. No.: 10/805,816

(22) Filed: Mar. 22, 2004

(65) Prior Publication Data

US 2005/0215898 A1    Sep. 29, 2005

(51) Int. Cl.
*A61B 8/00* (2006.01)

(52) U.S. Cl. .................. 600/437; 600/438; 600/485; 600/472; 367/7; 367/11; 367/130; 367/138; 128/916

(58) Field of Classification Search .............. 600/300, 600/437–472, 485; 367/7, 11, 130, 138; 128/916; 73/602–626
See application file for complete search history.

(56) References Cited

U.S. PATENT DOCUMENTS

| | | | |
|---|---|---|---|
| 3,885,551 A * | 5/1975 | Massie ................... 600/495 |
| 4,635,198 A * | 1/1987 | Hohlweck et al. ......... 600/448 |
| 5,031,627 A | 7/1991 | Yost et al. |
| 5,101,828 A * | 4/1992 | Welkowitz et al. ......... 600/481 |
| 5,150,620 A | 9/1992 | Allison |
| 5,214,955 A | 6/1993 | Yost et al. |
| 5,448,995 A | 9/1995 | Yost et al. |
| 5,569,853 A * | 10/1996 | Mignot ..................... 73/602 |
| 5,617,873 A | 4/1997 | Yost et al. |
| 5,746,209 A | 5/1998 | Yost et al. |
| 5,841,032 A | 11/1998 | Froggatt |
| 6,007,489 A | 12/1999 | Yost et al. |
| 6,308,715 B1 * | 10/2001 | Weissman et al. ........... 128/899 |
| 6,328,694 B1 * | 12/2001 | Michaeli .................... 600/438 |
| 6,413,227 B1 | 7/2002 | Yost et al. |
| 6,475,147 B1 | 11/2002 | Yost et al. |
| 6,526,309 B1 | 2/2003 | Chance |
| 6,702,743 B2 | 3/2004 | Michaeli |
| 6,740,048 B2 | 5/2004 | Yost et al. |
| 6,746,410 B2 | 6/2004 | Yost et al. |
| 6,761,695 B2 | 7/2004 | Yost et al. |
| 6,773,407 B2 | 8/2004 | Yost et al. |
| 2002/0095087 A1 | 7/2002 | Mourad et al. |

(Continued)

*Primary Examiner*—Brian L. Casler
*Assistant Examiner*—John F Ramirez
(74) *Attorney, Agent, or Firm*—Helen M. Galus

(57) ABSTRACT

A process and apparatus for measuring pressure buildup in a body compartment that encases muscular tissue. The method includes assessing the body compartment configuration and identifying the effect of pulsatible components on compartment dimensions and muscle tissue characteristics. This process is used in preventing tissue necrosis, and in decisions of whether to perform surgery on the body compartment for prevention of Compartment Syndrome. An apparatus is used for measuring pressure build-up in the body compartment having components for imparting ultrasonic waves such as a transducer, placing the transducer to impart the ultrasonic waves, capturing the imparted ultrasonic waves, mathematically manipulating the captured ultrasonic waves and categorizing pressure build-up in the body compartment from the mathematical manipulations.

23 Claims, 2 Drawing Sheets

U.S. PATENT DOCUMENTS

2002/0188206 A1* 12/2002 Davis et al. ................. 600/485
2003/0191409 A1   10/2003 Yost et al.
2006/0025686 A1*  2/2006 Ueno et al. ................. 600/443

* cited by examiner

ULTRASONIC APPARATUS AND METHOD TO ASSESS COMPARTMENT SYNDROME

JOINT GOVERNMENT EMPLOYEE AND SMALL BUSINESS OR NONPROFIT CONTRACTOR INVENTIONS

The inventions described herein were made as a result of activities undertaken within the scope of a cooperative agreement between the National Aeronautics and Space Administration and the University of California, San Diego, and is subject to the provisions of Public Law 96-517 (35 U.S.C. § 202) and may be manufactured and used by or for the Government for nmental purposes without the payment of any royalties thereon or therefor. In accordance with 35 U.S.C. 202, the contractor elected not to retain title.

FIELD OF THE INVENTION

The present invention provides novel processes, and apparatus for performing the processes, for interrogating a body compartment for compartment syndrome.

BACKGROUND AND DESCRIPTION OF THE RELATED ART

Compartment Syndrome, which may cause Volkmann's Ischemic Contracture, occurs when bleeding and swelling interfere with proper blood circulation in enclosed groups of muscles and nerves. In the body certain muscle groups, along with their associated blood vessels and nerve tissue, are covered by fascia, a noncompliant collagenous membrane, forming what is termed a "compartment." With bleeding and swelling, compartment pressure (CP) within the compartment increases, causing a decrease in venous, capillary and arterial blood flows. The network of blood vessels in the compartment becomes compressed by the pressure differential between the CP (exterior to the blood vessel) and the blood vessel interior, this impedes the rate of blood volume flow (RBFV) through the blood vessel network. Swelling occurs within the tissue, further restricting the blood flow. Although, according to the well-known Windkessel Theory, an occasional fluctuation in blood pressure pushes a bolus of blood through the blood vessel network, this normally is insufficient to reverse the continual deterioration of the muscle mass or maintain tissue viability. As the RBFV decreases to zero and as CP rises, muscles tend to tighten, contract and deteriorate, with both nerve and muscle cells eventually dying from the lack of nutrients. Compartment Syndrome creates acute pain and a progressive loss of muscle and nerve functions, usually in the lower leg and forearm, or possibly other body areas such as the wrist, buttocks, thigh and upper arm. As pressures build, blood flow becomes blocked, leading to permanent injury (Volkmann's Contracture) and possible amputation of the limb.

Compartment Syndrome most commonly occurs with trauma or substantial injury to the body, such as a broken or crushed arm or leg (frequently resulting in Acute Compartment Syndrome), with some occurrences of Compartment Syndrome coming from tight bandages or surgery (which can result in Acute Compartment Syndrome) or extended exercise (Chronic [exertional] Compartment Syndrome). After trauma to a given area, a person may experience pain or an inability to use the muscles in the injured area. Surgery, such as cutting the fascia, can be performed to decrease the compartment pressure and increase blood flow to the muscle. As the fascia is substantially inelastic, swelling increases pressure within the body compartment, and muscles, blood vessels and nerves within the compartment are compressed.

Even experienced physicians can have trouble making a reliable diagnosis of Compartment Syndrome. Known testing for Compartment Syndrome may include pressure measurement in the compartment by inserting a needle attached to a pressure meter. Compartment pressure of greater than 30-45 mmHg or pressures within 30 mmHg of the diastolic blood pressure, indicate the presence of Compartment Syndrome.

U.S. Pat. No. 5,746,209 to Yost et al., entitled "Method of and Apparatus for Histological Human Tissue Characterization Using Ultrasound" discloses the use of ultrasound for determining histological characteristics of tissue by converting the return of energy pulses into numerical terms, useful in a diagnosis for the development of pressure ulcers. However, Yost et al. '209 does not address the diagnosis of Compartment Syndrome.

There is a need in the art to provide a non-invasive determination of CP associated with Compartment Syndrome. The present invention addresses this and other needs.

BRIEF SUMMARY OF THE INVENTION

The present invention includes a process for measuring CP buildup in one or more body compartments that encase muscular tissue comprising the steps of assessing a body compartment configuration and identifying the effect of pulsatible components on the dimensions/geometry of the body compartment; and the present invention also includes a method for preventing tissue necrosis and an incision, as well as a non-incision product result from this process.

The present invention also includes an apparatus for assessing CP build-up in one or more body compartments that encase muscular tissue. This apparatus, depending upon the inventive embodiment being utilized, comprises one or more of the following: (a) a transmitting device for imparting ultrasonic waves into the one or more body compartments, (b) means for positioning the transducer adjacent to the one or more body compartments effective for imparting ultrasonic waves therein, (c) a receiver for capturing a series of reflections of the imparted ultrasonic waves from the interior of the tissue bounded by the compartment fascia, and converting these reflected waves into data, such as electrical signals, (d) means for mathematically manipulating the captured data, and (e) means for categorizing intra-muscular pressure build-up in the one or more body compartments from the mathematical manipulations.

In at least one embodiment, the present invention identifies dimensional changes in the blood flow network with pulsatile pressure changes to ascertain whether blood flow is adequate to assure tissue viability.

DETAILED DESCRIPTION OF THE EMBODIMENTS

The present invention provides a novel process and apparatus for interrogating a body compartment for Compartment Syndrome. Muscle groups in the arms and legs are encased in these body compartments that generally are defined by tubular shaped collagenous membranes as well as bone. At maximum distension the membrane loses compliance to the point that excessive CP can build up within the tissues confined by the membrane. A pathological condition, Compartment Syndrome, can develop because of such excess CP build-up. Body compartments also possess extensive networks of blood vessels, known as blood vessel networks (BVN), which typically obscure non-invasive methods of analysis due to the tubular shaped collagenous membranes. The present invention affords a method and means to ascertain the build-up of excessive pressures in compartments which encase muscle and muscle groups thereby warning medical practitioners of the existence of potentially dangerous medical conditions, which when allowed to persist, generally result in tissue necrosis.

Figure 1:
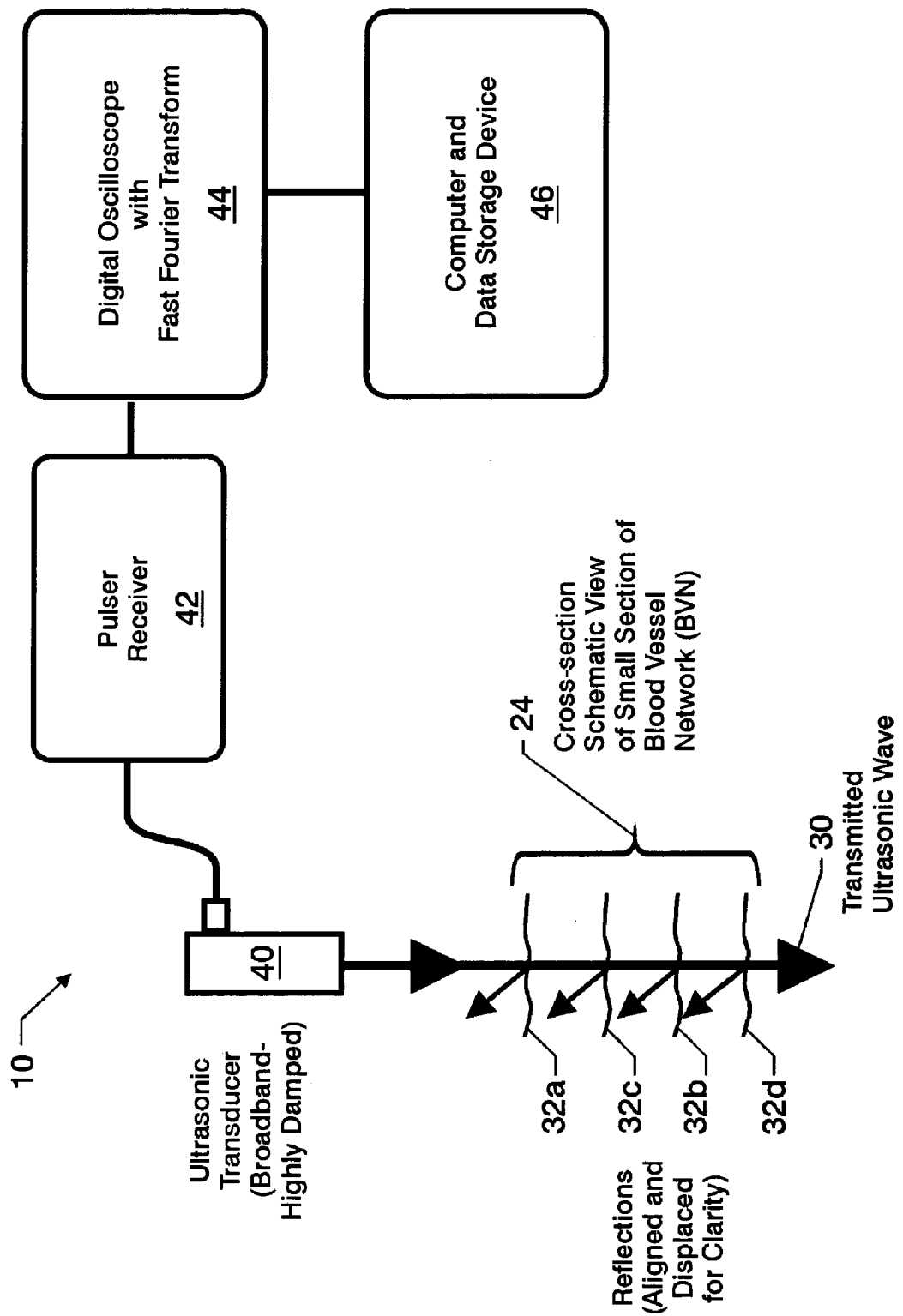
FIG. 1 is a schematic representation of apparatus of the present invention.

The process of the present invention measures CP buildup in one or more body compartments that encase muscular tissue by assessing a body compartment configuration and identifying the effect of pulsatile components (from the blood flow) on the dimensions of the body compartment. As seen in FIG. 1, the present invention includes an apparatus 10 for measuring pressure build-up in one or more body compartments 20 that encase muscular tissue. Referring to the schematic of FIG. 1, a representative equipment arrangement of the apparatus 10 in operation is shown. The apparatus 10 of the present invention includes a transducer 40 as a means for imparting ultrasonic waves 30 through the skin 22 (shown in FIG. 2), overlaying the body compartment 20. The transducer 40 includes a device by which energy can flow from one or more transmission systems to one or more other transmission systems. Transducer imparting devices 40 of the present invention may include a variety of known devices, for example, a broadband ultrasonic transmit/receiver transducer, pure-tone ultrasonic transmit/receiver transducer, and combinations thereof.

Figure 2:
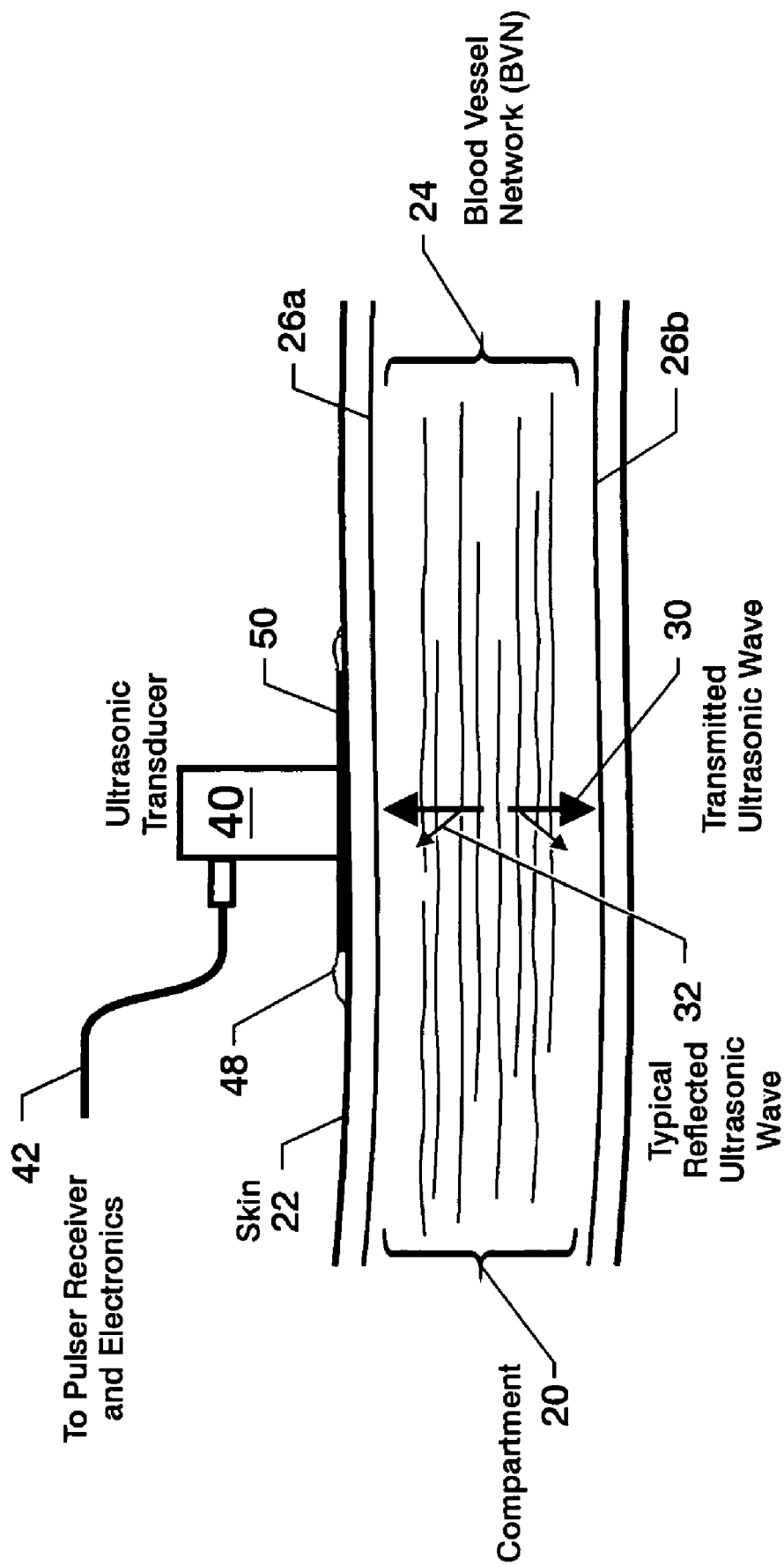
FIG. 2 is a schematic representation of ultrasonic interrogation of a body compartment of the present invention.

Referring now to FIG. 2, the transducer 40 is positionally located in a manner for effectively interrogating a body compartment 20 for Compartment Syndrome characterization thereof. Placement of the transducer 40 positions the release (imparting) of ultrasonic waves 30 into the body compartment 20 for obtaining relevant data related to the body compartment 20 from reflections 32 of the imparted ultrasonic waves 30 (FIG. 1). The means for effectively positioning the transducer 40 to obtain data from the reflections 32 of the imparted ultrasonic waves 30 allows capture of the reflected ultrasonic waves 32 from the body compartment 20, and retention and manipulation of data contained therein. One method of positioning the transducer 40 relative to the body compartment 20 includes placing the ultrasonic transducer 40 against the skin 22 of the extremity using a gel medium 48 for attaching the ultrasonic transducer 40 to the skin 22 adjacent to the body compartment 20. The gel medium 48 may serve as a couplant, and if needed, may be used to make a delay line for the ultrasonic wave transmission. Gel mediums 48 may include viscous substances that temporarily adhere the transducer 40 to the skin 22, such as those commonly known as ultrasound coupling gels. Additionally, for mechanical stability the transducer 40 may be inserted into the center of a disk 50, which can be taped, or otherwise secured, to a patient.

As seen in FIGS. 1 and 2, with the placement of the transducer 40 on the skin 22, and the generation of ultrasonic waves 30 into the body compartment 20, the imparted ultrasonic waves 30 are reflected (32) as they impinge on different surface layers within, and outside of, the body compartment 20, such as the compartment boundaries 26, identified as upper boundary 26A and lower boundary 26B, or BVN 24. The body compartment 20 may be placed at maximum distension prior to assessing the body compartment 20 configuration. As shown, the ultrasonic transducer 40 is further connected to a pulser-receiver system 42, with an appropriate electronics package, for fully utilizing the ultrasonic transducer 40 to investigate for Compartment Syndrome. Referring again to FIG. 1, these reflected waves 32 are captured for analysis by the pulser receiver 42 as a means to capture the reflected waves 32. Additionally, the means for capturing the imparted ultrasonic waves 30 may include any appropriate retention means 44, generally suited to a specific medical purpose. Representative retention means 44 include, for example without limitation, data storage, data display, data transmission, data analysis and/or combinations thereof. For example, emergency triage teams may use data display and/or data transmission to address urgent medical needs. Therapeutic centers may primarily use data comparisons for monitoring treatments. Data storage is preferably used in most medical situations for training, medical review and/or trend analysis. Computer manipulations, storage and other data methodologies using computer and data storage devices 46, or other like devices, may include data prior to, during and/or after mathematical manipulations, detailed below, are performed on the captured data. In at least one embodiment, the retention means 44 includes a digital oscilloscope with fast Fourier Transform capability detailed below.

The data obtained from the captured reflected ultrasonic waves 32 are mathematically manipulated to differentiate the separate layers of the body, both inside and outside of the body compartment 20. Mathematical manipulations include organization and processing of the data in any appropriate manner that defines these layers. Preferably, the mathematical manipulation of the captured ultrasonic waves includes Fourier Transform manipulation. The Fourier Transform manipulations of the data allow categorization of pressure build-up in the interrogated body compartment. As Compartment Syndrome is most prevalent in arms and/or legs, these body masses are typically investigated, although other body compartments 20 also may be interrogated for pressure buildup. Aspects of tissue characterization are described in U.S. Pat. No. 5,746,209 to Yost et al., entitled "Method of and Apparatus for Histological Human Tissue Characterization Using Ultrasound," the disclosure of which is hereby incorporated by reference as if set forth in its entirety herein.

With the transducer 40 positioned on, and transmitting ultrasonic waves 30 into, the skin 22, body compartments 20 are interrogated with the capture of the reflected ultrasonic waves 32. The apparatus 10 of the present invention can include either identifying a decrease in the captured imparted ultrasonic waves or identifying a ratio of low-frequency amplitudes to high frequency amplitudes present in the mathematical manipulation of the captured ultrasonic waves for categorization of the CP build-up.

In operation, as shown, the transducer 40 is energized with an electrical pulse which generates the ultrasonic pulse (UP) incorporating the ultrasonic wave 30. The UP 30 travels through the skin 22 and into the underlying tissues in the region of the compartment 20 as well as through the compartment 20, into the tissues contained by the compartment 20. Reflections 32 occur at each impedance discontinuity 32a, 32b, 32c, 32d, or each tissue interface, and are received at the transducer 40 in the sequence which they occur. The transducer 40 converts the ultrasonic sequence received back from the segment into an electrical sequence which can be amplified and sent to the oscilloscope to be digitized and displayed. For simplicity and speed of processing, the scope can perform and display the Fast Fourier Transform (FFT) on the sequence. Of note, the sequence and reflected sequence are partially regular over this segment, with this regularity showing on the FFT as a relatively larger amplitude of received signal at some specific frequency $f_1$. With the pressure in the compartment 20 within normal limits, the regularity of the sequence will be perturbed during heart beats, with this perturbation causing a change in the amplitude at $f_1$, indicating blood flow in the muscle tissue at those blood vessels which give rise to the constructive interference shown as a peak in the Fourier transform. If the pressure in the compartment 20 is sufficiently high, then flow through the BVN is impeded. During this condition the long term regularity is increased, and more peaks become prominent especially at the lower frequencies. Occasionally, and momentarily, the order disappears from the FFT, only for the order to return. This permits the Windkessel condition to be identified and timed. If these disturbances are non-existent, or occur too infrequently, then tissue viability is at risk, and surgical intervention may be needed.

The FFT and the temporal sequence can be stored for future reference and for interpretation. The system may be set in an algorithm which automatically identifies the conditions. The system may be incorporated into a monitor which would be capable of logging the circulation condition within a compartment, and placed within a system for scanning to explore the state of circulation within the compartment.

In one embodiment, determination of the presence or absence of Compartment Syndrome occurs with identification of the BVN and the effect of pulsatile components on the geometry of the BVN. Operation of the Fourier Transform manipulations provides identification of the net geometry through the pulsating frequency components. An analysis based on the pulsating components showing a decrease or diminishment of the pulsations indicates a pressure build-up.

In another embodiment, a time-reversal technique is incorporated as a means to identify changes in the compartment as blood vessel pulsations occur. As the broadband ultrasonic transducer 40 is activated with a voltage spike, the received signal is recorded and then reversed in time and played back to the transducer 40. The new signal received from the time-reversed signal from the previous step produces a spike, when received, unless there has been a change in the body compartment 20. As such, by monitoring the reversed play-back signal and noting variations from the spike, changes in compartment dynamics affecting the shape of the spike can be identified. Shape changes in the spike become readily identifiable and can be analyzed through mathematical manipulations, such as FFT. With the absence of Compartment Syndrome, the spike provides a flat FFT. Hence by noting variations in the FFT, changes in conditions within the body compartment 20 are identified, and a practitioner monitoring for Compartment Syndrome may be alerted. Additional analysis of the FFT of the spike permits the determination of the type of change that could occur, and/or has occurred in the compartment 20.

Using the inventive processes for monitoring the indication of CP buildup, prevention of tissue necrosis is possible. With the determination of the presence of Compartment Syndrome, corrective or preventive actions may be performed, such as cutting (slitting) the fascia to relieve the excessive CP. Conversely, when the absence of compartment syndrome is determined, detrimental actions such as cutting an incision may be avoided. This non-incision determination prevents unnecessary medical treatment, further benefiting the muscle function and health of a patient.

The foregoing summary, description, and examples of the present invention are not intended to be limiting, but are only exemplary of the inventive features which are defined in the claims.

What is claimed is:

1. A process for measuring pressure buildup in one or more body compartments that encases muscular tissue, comprising the steps of:
    transmitting ultrasonic waves into a body compartment;
    capturing a sequence of reflections of the transmitted ultrasonic waves;
    converting the ultrasonic sequence into an electrical sequence;
    mathematically manipulating the electrical sequence such that amplitude changes of the manipulated sequence, at a substantially constant frequency, correspond to phase changes of the ultrasonic sequence;
    analyzing amplitude changes of the manipulated sequence to identify the effect of pulsatile components on at least one surface layer of the body compartment; and
    categorizing pressure build up in the body compartment based on the identified effect.

2. The process of claim 1, wherein the step of mathematically manipulating the electrical sequence includes the step of identifying characteristics of the body compartment selected from the group consisting of the blood vessel network, compartment boundary and combinations thereof 3. The process of claim 2, wherein the step of identifying characteristics of the body compartment comprises identifying blood vessel network characteristics of the body compartment through a broadband ultrasonic transmit/receive transducer.

4. The process of claim 2, wherein the step of identifying characteristics of the body compartment comprises identifying compartment boundary characteristics of the body compartment through a pure-tone ultrasonic transmit/receive transducer.

5. The process of claim 1, wherein the step of capturing a sequence of reflections includes means for capturing temporal reception of ultrasonic waves.

6. The process of claim 5, wherein the step of mathematically manipulating the electrical sequence such that amplitude changes of the manipulated sequence, at a substantially constant frequency, correspond to phase changes of the ultrasonic sequence comprises utilizing the Fourier Transform method.

7. The process of claim 1, further comprising the step of placing the body compartment at maximum distension prior to assessing the body compartment configuration.

8. The process of claim 1, wherein the body compartment comprises a tubular shaped collagenous membrane selected from the group consisting of arm, leg, other muscle groups and combinations thereof 9. A method for preventing tissue necrosis comprising the process of claim 1.

10. The process of claim 1 further comprising the step of alleviating at least a portion of the pressure build up through the use of an incision product.

11. The process of claim 1 further comprising the step of alleviating at least a portion of the pressure build up through the use of a non incision product.

12. An apparatus for non-invasively measuring pressure build-up in one or more body compartments that encase muscular tissue, comprising:
    (a) a transmitting device for imparting ultrasonic waves into one or more body compartments that are not being subjected to externally applied blood flow occluding pressure;
    (b) means for positioning the transmitting device adjacent to the one or more body compartments effective for imparting the ultrasonic waves therein;

(c) means for capturing reflections of the imparted ultrasonic waves and converting the reflected waves into electrical signals;

(d) means for mathematically manipulating the electrical signals; and, (e) means for categorizing pressure build-up in the one or more body compartments from the mathematical manipulations.

13. The apparatus of claim 12, wherein the transmitting device comprises a transducer.

14. The apparatus of claim 12, wherein the means for placing the transducer comprises a gel.

15. The apparatus of claim 12, wherein the means for capturing comprises a retention means selected from the group consisting of storage, display, analysis and combinations thereof 16. The apparatus of claim 12, wherein the mathematical manipulation of the electrical signals comprises Fourier Transform manipulation.

17. The apparatus of claim 12, wherein the means for categorizing pressure build-up further comprises means for identifying a decrease in the captured imparted ultrasonic waves.

18. The apparatus of claim 12, wherein the means for categorizing pressure build-up further comprises means for identifying a ratio of low-frequency amplitudes to high frequency amplitudes present in the mathematical manipulation.

19. The apparatus of claim 12, wherein categorizing pressure build-up in one or more body compartment comprises a body compartment selected from the group consisting of arms, legs, other muscle groups and combinations thereof 20. The apparatus of claim 12, wherein the means for capturing comprises a receiver.

21. The apparatus of claim 12, wherein the means for categorizing pressure build-up comprises means for assessing a body compartment configuration and identifying the effect of pulsatile components on at least one dimension of the body compartment.

22. The apparatus of claim 21, wherein the means for categorizing pressure build-up further comprises a time-reversal technique.

23. An apparatus for non-invasively measuring pressure build-up in one or more body compartments that encase muscular tissue comprising:

(a) a transmitting device for imparting ultrasonic waves into one or more body compartments that are not being subjected to externally applied blood flow occluding pressure;

(b) means for positioning the transmitting device adjacent to the one or more body compartments effective for imparting the ultrasonic waves therein;

(c) a receiver for capturing reflections of the imparted ultrasonic waves;

(d) means for mathematically manipulating the ultrasonic waves captured by the receiver; and, (e) means for categorizing pressure build-up in the one or more body compartments from the mathematical manipulations.

* * * * *